United States Patent
Kawakami et al.

(10) Patent No.: US 9,421,299 B2
(45) Date of Patent: Aug. 23, 2016

(54) MEDICAL ADHESIVE

(75) Inventors: Naoaki Kawakami, Kyoto (JP); Hiroaki Maeda, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 23 days.

(21) Appl. No.: 14/005,906

(22) PCT Filed: Mar. 9, 2012

(86) PCT No.: PCT/JP2012/056179
§ 371 (c)(1),
(2), (4) Date: Oct. 3, 2013

(87) PCT Pub. No.: WO2012/128086
PCT Pub. Date: Sep. 27, 2012

(65) Prior Publication Data
US 2014/0018510 A1 Jan. 16, 2014

(30) Foreign Application Priority Data
Mar. 22, 2011 (JP) ................. 2011-062892

(51) Int. Cl.
*A61L 24/04* (2006.01)
*C09J 175/04* (2006.01)
*C09J 175/08* (2006.01)
*C08G 18/48* (2006.01)
*C08G 18/77* (2006.01)

(52) U.S. Cl.
CPC ........... *A61L 24/046* (2013.01); *C08G 18/4837* (2013.01); *C08G 18/4845* (2013.01); *C08G 18/773* (2013.01); *C09J 175/04* (2013.01); *C09J 175/08* (2013.01)

(58) Field of Classification Search
CPC ..... A61L 24/046; C09J 175/04; C09J 175/08; C08G 18/4837; C08G 18/4845; C08G 18/773
See application file for complete search history.

(56) References Cited

U.S. PATENT DOCUMENTS

| 4,994,542 A | 2/1991 | Matsuda et al. |
| 2005/0131192 A1 | 6/2005 | Matsuda et al. |
| 2010/0249450 A1 | 9/2010 | Maebe et al. |

FOREIGN PATENT DOCUMENTS

| EP | 1741454 A1 * | 1/2007 | .............. A61L 24/04 |
| JP | S57-108055 | 7/1982 | |
| JP | H01-227762 | 9/1989 | |
| JP | 6-41044 | 2/1994 | |
| JP | 2000-005296 | 1/2000 | |
| JP | 2002-201443 | 7/2002 | |
| JP | 2004-261590 | 9/2004 | |
| JP | 2005-015537 | 1/2005 | |
| JP | 2005-124808 | 5/2005 | |
| JP | 2009-006140 | 1/2009 | |
| JP | 2010-254764 | 11/2010 | |
| WO | 03/051952 | 6/2003 | |
| WO | 2009/063828 | 5/2009 | |

OTHER PUBLICATIONS

"Synthesis of Fluorinated Diisocyanates" Malik et al., J.Org.Chem. 1991, 56, 3043-3044.*
International Preliminary Report on Patentability issued Sep. 24, 2013 in corresponding International Application No. PCT/JP2012/056179.
Synthesis of Fluorinated Polyurethanes, Journal of Macromolecular Science, Physics, B1(4), 1967, p. 831-850.

* cited by examiner

*Primary Examiner* — Michael L Leonard
(74) *Attorney, Agent, or Firm* — Wenderoth, Lind & Ponack, L.L.P.

(57) ABSTRACT

The present invention is directed to providing a safe medical adhesive, a cured body of which is hard to be degraded and decomposed and thus stable and the cured body generates less amount of acid, aldehyde, etc. due to degradation/decomposition. The medical adhesive includes a hydrophilic urethane prepolymer (UP) obtained by reacting a polyisocyanate component (A) containing a fluorine-containing non-aromatic polyisocyanate compound (A1) as an essential ingredient and a polyol component (B) containing a hydrophilic polyol (B1) as an essential ingredient, wherein a chlorine content in a chlorine-containing organic compound based on the weight of the hydrophilic urethane prepolymer (UP) is 0.005 wt % or less.

7 Claims, No Drawings

MEDICAL ADHESIVE

TECHNICAL FIELD

The present invention relates to a medical adhesive.

BACKGROUND ART

As a medical adhesive for bonding body tissues such as blood vessel, heart, respiratory organ and digestive organ, using e.g., a hydrophilic urethane prepolymer having isocyanate group in terminal(s) of itself, which is obtained by the reaction between a fluorine-containing polyisocyanate and a hydrophilic polyether polyol, has been conventionally known (Patent Literatures 1 and 2).

However, a cured body (polymerized product through a reaction with water) obtained by curing a conventional medical adhesive using a fluorine-containing polyisocyanate has a problem in that it degrades and decomposes with time and its adhesive strength easily decreases. In the circumstances, a method of preventing reduction of adhesive strength by reducing the hydrolytic chlorine content in a fluorine-containing polyisocyanate is known (Patent Literature 3).

CITATION LIST

Patent Literature

Patent Literature 1: JP 1-227762 A
Patent Literature 2: International Publication No. WO03/051952
Patent Literature 3: JP 2005-124808 A

SUMMARY OF INVENTION

Technical Problem

However, even if the hydrolytic chlorine content is reduced, the cured body of a medical adhesive can be degraded and decomposed with time.
Degradation/decomposition cannot be always prevented at present.
An object of the present invention is to provide a safe medical adhesive, a cured body of which is hard to be degraded and decomposed and thus stable and the cured body generates less amount of carboxylic acid, aldehyde, etc. due to degradation/decomposition.

Solution to Problem

The present inventors found that the sum of chlorine contents in chlorine-containing organic compounds in a hydrophilic urethane prepolymer has an extremely large effect on the stability of the cured body, and reached the present invention.

In summary, the medical adhesive of the present invention includes a hydrophilic urethane prepolymer (UP) obtained by reacting a polyisocyanate component (A) including a fluorine-containing non-aromatic polyisocyanate compound (A1) as an essential ingredient and a polyol component (B) including a hydrophilic polyol (B1) as an essential ingredient, wherein a chlorine content in a chlorine-containing organic compound based on the weight of the hydrophilic urethane prepolymer (UP) is 0.005 wt % or less, and the chlorine content in the chlorine-containing organic compound is a sum of chlorine contents in the following compounds (1) to (14), a reaction product between compound (1) and (B), a reaction product between compound (2) and (B), a reaction product between compound (7) and (B) and a reaction product between compound (8) and (B).

Compound (1): A compound represented by the following general formula (I). In the general formula (I), n represents an integer of 1 to 20.

$$OCNCH_2(CF_2)_nCH_2OCOCl \quad (I)$$

Compound (2): A compound represented by the following general formula (II). In the general formula (II), n represents an integer of 1 to 20.

$$OCNCH_2(CF_2)_nCH_2Cl \quad (II)$$

Compound (3): A compound represented by the following general formula (III). In the general formula (III), n represents an integer of 1 to 20.

$$ClOCOCH_2(CF_2)_nCH_2OCOCl \quad (III)$$

Compound (4): A compound represented by the following general formula (IV). In the general formula (IV), n represents an integer of 1 to 20.

$$ClCH_2(CF_2)_nCH_2Cl \quad (IV)$$

Compound (5): A compound represented by the following general formula (V).

$$O(CH_2CH_2Cl)_2 \quad (V)$$

Compound (6): A compound represented by the following general formula (VI).

$$ClOCO(CH_2CH_2OCH_2)_2OCH_3 \quad (VI)$$

Compound (7): A compound represented by the following general formula (VII). In the general formula (VII), n represents an integer of 1 to 22.

$$OCN(CF_2)_nOCOCl \quad (VII)$$

Compound (8): A compound represented by the following general formula (VIII). In the general formula (VIII), n represents an integer of 1 to 22.

$$OCN(CF_2)_nCl \quad (VIII)$$

Compound (9): A compound represented by the following general formula (IX). In the general formula (IX), n represents an integer of 1 to 22.

$$ClOCO(CF_2)_nOCOCl \quad (IX)$$

Compound (10): A compound represented by the following general formula (X). In the general formula (X), n represents an integer of 1 to 22.

$$Cl(CF_2)_nCl \quad (X)$$

Compound (11): A compound represented by the following general formula (XI).

$$O(CH_2CH_2OCOCl)_2 \quad (XI)$$

Compound (12): A compound represented by the following general formula (XII).

$$ClOCOCH_2CH_2OCH_2CH_2OCOCl \quad (XII)$$

Compound (13): A compound represented by the following general formula (XIII).

$$ClCH_2CH_2OCH_2CH_2OCOCl \quad (XIII)$$

Compound (14): A compound represented by the following general formula (XIV).

$$ClCH_2CH_2OCH_2CH_2OCH_3 \qquad (XIV)$$

Advantageous Effects of Invention

The medical adhesive of the present invention is excellent in stability since a cured body, which is obtained by curing the adhesive, is hard to be degraded and decomposed with time. In addition, the medical adhesive of the present invention is highly safe since carboxylic acid and aldehyde do not generate.

DESCRIPTION OF EMBODIMENTS

In the present invention, a polyisocyanate component (A) includes a fluorine-containing non-aromatic polyisocyanate compound (A1) as an essential ingredient; however, e.g., a fluorine atom-free polyisocyanate compound (A2) and a fluorine-containing aromatic polyisocyanate compound (A3) may be used in combination.

As the fluorine-containing non-aromatic polyisocyanate compound (A1), e.g., a fluorine-containing aliphatic diisocyanate (A11) having 3 to 24 carbon atoms, a fluorine-containing alicyclic diisocyanate (A12) having 8 to 21 carbon atoms and a fluorine-containing poly-(3 to 6 valent) isocyanate (A13) having 9 to 72 carbon atoms can be used.

Examples of the fluorine-containing aliphatic diisocyanate (A11) having 3 to 24 carbon atoms include a compound represented by OCN—Rf-NCO (Rf represents a perfluoroalkylene group having 1 to 22 carbon atoms) and a compound represented by OCN—CH$_2$—Rf-CH$_2$—NCO (Rf represents a perfluoroalkylene group having 1 to 20 carbon atoms).

Examples of the compound represented by OCN—Rf-NCO include difluoromethylene diisocyanate, perfluorodimethylene diisocyanate, perfluorotrimethylene diisocyanate, perfluorooctyl diisocyanate and perfluoroeicosylene diisocyanate.

Examples of the compound represented by OCN—CH$_2$—Rf-CH$_2$—NCO include bis(isocyanatomethyl)difluoromethane, bis(isocyanatomethyl)perfluoroethane, bis(isocyanatomethyl)perfluoropropane, bis(isocyanatomethyl) perfluorobutane, bis(isocyanatomethyl)perfluoropentane, bis (isocyanatomethyl)perfluorohexane, and bis (isocyanatomethyl)perfluoroeicosane.

Examples of the fluorine-containing alicyclic diisocyanate (A12) having 8 to 21 carbon atoms include diisocyanatoperfluorocyclohexane, bis(isocyanatomethyl)perfluorocyclohexane, bis(isocyanatomethyl)perfluorodimethylcyclohexane, bis(isocyanatoperfluorocyclohexyl)perfluoropropane, and bis(isocyanatomethylperfluorocyclohexyl)perfluoropropane.

Examples of the fluorine-containing poly-(3 to 6 valent) isocyanate (A13) having 9 to 72 carbon atoms include isocyanurate compounds derived from the aforementioned diisocyanates, adduct compounds derived from the aforementioned diisocyanates and tris(isocyanatotetrafluorocyclohexyl)methane.

Note that an isocyanate group in a fluorine-containing non-aromatic polyisocyanate compound (A1) is preferably present at a position rarely undergoing sterical hindrance, in view of e.g., the reactivity with a polyol component (B) and the reactivity with e.g., blood and body fluid, and further preferably present at a terminal position thereof rarely undergoing sterical hindrance.

Furthermore, a fluorine-containing non-aromatic polyisocyanate compound (A1) may be a single compound or a mixture of two or more compounds.

Furthermore, of the fluorine-containing non-aromatic polyisocyanate compounds (A1), a compound having two isocyanate groups is preferable since, for example, a side reaction such as a crosslinking reaction should be hard to occur.

Of the fluorine-containing non-aromatic polyisocyanate compounds (A1), a fluorine-containing aliphatic polyisocyanate (A11) is preferable in view of e.g., safety such as mutagenicity. Further preferably, a fluorine-containing aliphatic polyisocyanate represented by OCN—CH$_2$—Rf-CH$_2$—NCO and a fluorine-containing aliphatic polyisocyanate represented by OCN—Rf-NCO are mentioned, and particularly preferably, difluoromethylene diisocyanate, perfluorodimethylene diisocyanate, perfluorotrimethylene diisocyanate, perfluorooctyl diisocyanate, perfluoroeicosylene diisocyanate, bis(isocyanatomethyl)perfluoropropane, bis (isocyanatomethyl)perfluorobutane, bis(isocyanatomethyl) perfluoropentane and bis(isocyanatomethyl)perfluorohexane are mentioned.

As the fluorine atom-free polyisocyanate compound (A2), e.g., a fluorine atom-free aliphatic polyisocyanate (A21) having 1 to 24 carbon atoms, a fluorine atom-free alicyclic polyisocyanate (A22) having 8 to 21 carbon atoms, a fluorine atom-free araliphatic polyisocyanate (A23) having 8 to 21 carbon atoms, a fluorine atom-free aromatic polyisocyanate (A24) having 8 to 21 carbon atoms and modified compounds (A25) of these can be used.

Examples of the fluorine atom-free aliphatic polyisocyanate (A21) include tetramethylene diisocyanate, hexamethylene diisocyanate (HDI), 2,2,4-trimethylhexamethylene diisocyanate and lysine diisocyanate.

Examples of the fluorine atom-free alicyclic polyisocyanate (A22) include isophorone diisocyanate (IPDI), dicyclohexylmethane-4,4'-diisocyanate (hydrogenated MDI), cyclohexylene diisocyanate and methylcyclohexylene diisocyanate (hydrogenated TDI).

Examples of the fluorine atom-free araliphatic polyisocyanate (A23) include m- or p-xylylene diisocyanate (XDI) and α,α,α',α'-tetramethylxylylene diisocyanate (TMXDI).

Examples of the fluorine atom-free aromatic polyisocyanate (A24) include 1,3- or 1,4-phenylene diisocyanate (PDI), 2,4- or 2,6-tolylene diisocyanate (TDI), 2,4'- or 4,4'-diphenylmethane diisocyanate (MDI) and crude MDI.

Furthermore, examples of modified compounds (A25) of these include a urethane modified compound, an isocyanurate modified compound, an allophanate modified compound, a biuret modified compound, a uretdione modified compound, a uretoneimine modified compound and a uretdione/isocyanurate modified compound. Examples of a modified HDI compound include a urethane modified HDI, a carbodiimide modified HDI and a trihydrocarbyl phosphate modified HDI. Examples of a modified MDI compound include a urethane modified MDI and a carbodiimide modified MDI. Examples of a modified TDI compound include a urethane modified TDI and a carbodiimide modified TDI.

Note that a fluorine atom-free polyisocyanate compound (A2) may be a single compound or a mixture of two or more compounds.

Of these polyisocyanate compounds (A2), a fluorine atom-free aromatic polyisocyanate (A24) is preferable in view of e.g., reactivity and further preferably an MDI and a TDI are mentioned.

Furthermore, in view of safety, a fluorine atom-free aliphatic polyisocyanate (A21) is preferable and an HDI is further preferable.

When a fluorine atom-free polyisocyanate compound (A2) is used, in view of e.g., safety such as mutagenicity, the content (wt %) of (A2) based on the weight of a fluorine-containing non-aromatic polyisocyanate compound (A1) is preferably 0.1 to 20, further preferably 0.2 to 10, and particularly preferably 0.3 to 5.

As the fluorine-containing aromatic polyisocyanate compound (A3), e.g., a fluorine-containing aromatic polyisocyanate prepared by partly or wholly substituting the hydrogen atoms of the aromatic ring(s) in a fluorine atom-free aromatic polyisocyanate (A24) with fluorine atoms, can be used.

A fluorine-containing aromatic polyisocyanate (A31) is prepared by substituting all hydrogen atoms of the aromatic ring(s) with fluorine atoms. Specific examples thereof include 1,3- or 1,4-perfluorophenylene diisocyanate, 3,5,6- or 3,4,5-trifluoro-2,4- or 2,6-tolylene diisocyanate and tetrafluoro-2, 4'- or 4,4'-diphenylmethane diisocyanate.

A fluorine-containing aromatic polyisocyanate (A32) is prepared by substituting a part of hydrogen atoms of the aromatic ring(s) with fluorine atoms. Specific examples thereof include a trifluoromethyl-monofluoro-phenylene-1,3 or 1,4-diisocyanate and 2,4'- or 4,4'-diphenyldifluoromethane diisocyanate.

A fluorine-containing aromatic polyisocyanate (A33) is prepared by substituting all hydrogen atoms with fluorine atoms. Specific examples thereof include 2,4- or 2,6-perfluorotolylene diisocyanate and 2,4'- or 4,4'-perfluorodiphenylmethane diisocyanate.

Note that a fluorine-containing aromatic polyisocyanate compound (A3) may be a single compound or a mixture of two or more compounds.

Of these fluorine-containing aromatic polyisocyanate compounds (A3), in view of e.g., reactivity, a fluorine-containing aromatic polyisocyanate (A31) and a fluorine-containing aromatic polyisocyanate (A33), which are prepared by at least partly or wholly substituting hydrogen atoms of the aromatic ring(s) with fluorine atoms, are preferable; and further preferably, a fluorine-containing aromatic polyisocyanate (A33) is mentioned.

When a fluorine-containing aromatic polyisocyanate compound (A3) is used, in view of e.g., safety such as mutagenicity, the content (wt %) of (A3) based on the weight of a fluorine-containing non-aromatic polyisocyanate compound (A1) is preferably 0.1 to 5, further preferably 0.2 to 3, and particularly preferably 0.3 to 2.

The content (wt %) of hydrolytic chlorine in a polyisocyanate component (A) based on the weight of (A) is preferably 0.05 or less, further preferably 0.04 or less, and still further preferably 0.03 or less. If the hydrolytic chlorine content falls within the range, it is possible to provide a medical adhesive hard to be colored and hard to be changed in wet adhesive strength upon y ray irradiation (about 25 kGy) indispensable for sterilization of a medical adhesive.

Furthermore, the content (wt %) of hydrolytic chlorine in a medical adhesive based on the weight of a hydrophilic urethane prepolymer (UP) is preferably 0.015 or less and further preferably 0.010 or less, in view of colorability and wet adhesiveness.

The hydrolytic chlorine is conceivably ascribed to raw materials (unreacted compounds) and an intermediate for producing a polyisocyanate and impurities such as hydrogen chloride, phosgene, triphosgene, carbamyl chloride, chloroformate, benzyl chloride, carbodiimide and carbamoyl chloride.

Note that the hydrolytic chlorine content is measured in accordance with JISK1603-3: 2007.

In the present invention, a polyol component (B), which is a component including a hydrophilic polyol (B1) as an essential ingredient, may include other polyols (B2) having low hydrophilicity.

Examples of the hydrophilic polyol (B1) include a polyol having an oxyethylene group content of 30 to 100 wt % based on the weight of (B1), and e.g., a polyether polyol (B1-1) containing an oxyethylene group and a polyester polyol (B1-2) obtained from (B1-1) as an essential ingredient can be used.

The solubility parameter (SP value) of a hydrophilic polyol (B1) preferably falls within the range of 7 to 17 and further preferably 8 to 16, in view of reactivity and adhesive strength.

Furthermore, the HLB of a hydrophilic polyol (B1) is preferably 4 to 20 and further preferably 4.5 to 20, in view of reactivity and adhesive strength.

Herein, the term "HLB" refers to an index showing balance between hydrophilicity and lipophilicity and can be calculated from a ratio of the organicity value and the inorganicity value of an organic compound, in accordance with the Oda method described, for example, in "Introduction to Surfactants" [written by Takehiko Fujimoto, issued by Sanyo Chemical Industries, Ltd. in 2007], page 212.

$$HLB \approx 10 \times inorganicity/organicity$$

The organicity and inorganicity values for obtaining HLB can be calculated from values listed in the table described on page 213 in the "Introduction to Surfactants."

As a polyether polyol (B1-1) containing an oxyethylene group, e.g., an ethylene oxide adduct to a compound having at least two active hydrogen atoms or a co-adduct of ethylene oxide and an alkylene oxide having 3 to 8 carbon atoms (e.g., 1,2- or 1,3-propylene oxide, 1,2-, 1,3-, 2,3- or 1,4-butylene oxide and styrene oxide) can be used. In the case of a co-adduct, the addition manner may be random, block and a mixture of these; however random addition is preferable in view of adhesive strength.

Furthermore, as the alkylene oxide having 3 to 8 carbon atoms, 1,2-propylene oxide is preferable in view of adhesive strength.

As the compound having at least two active hydrogen atoms, e.g., water, a diol, a polyol of 3 to 8 valences, a dicarboxylic acid, a polycarboxylic acid of 3 to 4 valences, a monoamine, a polyamine and a polythiol can be used.

Note that when a compound having two active hydrogen atoms is used, a divalent hydrophilic polyol is obtained. When a compound having three or more active hydrogen atoms is used, a hydrophilic polyol of trivalence or more is obtained.

As the diol, e.g., an alkylene glycol having 2 to 30 carbon atoms (e.g., ethylene glycol, 1,2-propylene glycol, 1,3-propylene glycol, 1,4-butane diol, 1,6-hexane diol, octane diol, decane diol, dodecane diol, tetradecane diol, neopentyl glycol and 2,2-diethyl-1,3-propanediol); an alicyclic diol having 6 to 24 carbon atoms (e.g., 1,4-cyclohexane dimethanol and hydrogenated bisphenol A); a bisphenol having 15 to 30 carbon atoms (e.g., bisphenol A, bisphenol F and bisphenol S); and dihydroxybenzene (e.g., catechol and hydroquinone) can be used.

As the polyol of 3 to 8 valences, e.g., an aliphatic polyhydric alcohol having 3 to 8 carbon atoms (e.g., glycerin, trimethylolethane, trimethylolpropane, pentaerythritol, sorbitan, diglycerol and sorbitol) can be used.

As the dicarboxylic acid, e.g., an alkane dicarboxylic acid having 4 to 32 carbon atoms (e.g., succinic acid, adipic acid, sebacic acid, azelaic acid, sebacic acid, dodecane dicarboxylic acid, octadecane dicarboxylic acid, dodecyl succinic acid and octadecyl succinic acid); an alkene dicarboxylic acid having 4 to 32 carbon atoms (e.g., maleic acid, fumaric acid, citraconic acid, mesaconic acid, dimer acid, dodecenyl succinic acid and pentadecenyl succinic acid); and an aromatic dicarboxylic acid having 8 to 20 carbon atoms (e.g., phthalic acid, isophthalic acid, terephthalic acid and naphthalene dicarboxylic acid) can be used. Other than these, e.g., an anhydride of a dicarboxylic acid (e.g., maleic anhydride and phthalic anhydride) and a lower alkyl (1 to 4 carbon atoms) ester (e.g., methyl ester, ethyl ester, isopropyl ester and t-butyl ester) can be also used.

As the polycarboxylic acid of 3 to 4 valences, e.g., aromatic polycarboxylic acid having 9 to 20 carbon atoms (e.g., trimellitic acid and pyromellitic acid) can be used. Other than these, e.g., a polycarboxylic acid anhydride (e.g., trimellitic anhydride and pyromellitic anhydride) and a lower alkyl (1 to 4 carbon atoms) ester (e.g., methyl ester, ethyl ester and isopropyl ester) can be also used.

As the monoamine, e.g., an ammonia and an aliphatic primary amine having 1 to 20 carbon atoms {e.g., an alkyl amine having 1 to 20 carbon atoms (e.g., methylamine, ethylamine, propylamine, hexylamine, dodecylamine and eicosyl amine)}; an alicyclic amine having 4 to 15 carbon atoms (e.g., piperidine, aminocyclohexane, isophorone monoamine and 4-methylene dicyclohexane monoamine); and an aromatic-ring containing aliphatic amine having 6 to 15 carbon atoms (e.g., benzylamine) can be used.

As the polyamine, e.g., an aliphatic polyamine having 2 to 18 carbon atoms {e.g., an alkylenediamine having 2 to 12 carbon atoms (e.g., ethylenediamine, propylenediamine, trimethylenediamine, hexamethylenediamine, N,N'-diethylethylenediamine and undecylenediamine) and a polyalkylene (2 to 6 carbon atoms) polyamine (e.g., diethylenetriamine, dipropylenetriamine, triethylenetetramine and pentaethylenenhexamine)}; an alicyclic polyamine having 4 to 15 carbon atoms (e.g., 1,3-diaminocyclohexane, isophorone diamine and 4,4'-methylenedicyclohexanediamine); and a heterocyclic polyamine having 4 to 15 carbon atoms (e.g., piperazine, N-aminoethylpiperazine, 1,4-diaminoethylpiperazine and N-aminoethylpyridine) can be used.

As the polythiol, e.g., dithiol having 2 to 24 carbon atoms (e.g., ethanedithiol, 1,4-butanedithiol and 1,6-hexanedithiol) and a polythiol of 3 to 6 valences having 5 to 3000 carbon atoms [e.g., trade name: Capcure 3800 (manufactured by Japan Epoxy Resins Co., Ltd.) and polyvinylthiol] can be used.

As the compound having at least two active hydrogen atoms, other than the aforementioned ones, e.g., an amino acid, an oxycarboxylic acid and an amino alcohol can be also used.

A compound having at least two active hydrogen atoms may be a single compound or a mixture of two or more compounds.

As the compound having at least two active hydrogen atoms, water and a diol are preferable in view of safety to a living body and adhesive strength; further preferably, water and an alkylene glycol are mentioned; and particularly preferably water and an alkylene glycol having 2 to 4 carbon atoms are mentioned.

Preferable examples of a polyether polyol (B1-1) containing an oxyethylene group include an ethylene oxide adduct to a diol (e.g., ethylene oxide adduct to ethylene glycol and an ethylene oxide adduct to propylene glycol) and a co-adduct of ethylene oxide and an alkylene oxide having 3 to 8 carbon atoms to a diol (e.g., a random or block co-adduct of ethylene oxide and propylene oxide to ethylene glycol and a random or block co-adduct of ethylene oxide and butylene oxide to ethylene glycol).

As the polyether polyol (B1-1), an ethylene oxide adduct to a diol and a co-adduct of ethylene oxide and propylene oxide to a diol are preferable, since the reactivity to water increases and e.g., a further satisfactory adhesive strength is obtained; and particularly preferably, a co-adduct of ethylene oxide and propylene oxide to a diol is mentioned.

A polyether polyol (B1-1) may be a single compound or a mixture of two or more compounds.

The hydroxyl-group equivalent of a polyether polyol (B1-1) (the number average molecular weight of a polyether polyol (B1-1) per hydroxyl group) is preferably 50 to 5000, further preferably 100 to 4000, and particularly preferably 200 to 3000. If the hydroxyl-group equivalent falls within the range, e.g., further satisfactory adhesive strength is obtained.

Note that the hydroxyl-group equivalent is determined in accordance with JIS K1557-1: 2007.

As the polyester polyol (B1-2) obtained from a polyether polyol (B1-1) as an essential ingredient, e.g., a polyester between a polyether polyol (B1-1) and a dicarboxylic acid, a dicarboxylic acid anhydride, and/or a dicarboxylic acid lower alkyl ester as mentioned in the above section of a compound having at least two active hydrogen atoms can be used. These polyesters each are terminated with a hydroxyl group.

Note that, as a part of a dicarboxylic acid, a dicarboxylic acid anhydride and/or a dicarboxylic acid lower alkyl ester, e.g., a polycarboxylic acid, a polycarboxylic acid anhydride and a polycarboxylic acid lower alkyl ether can be also used. When these are used, the use amount (mole %) of these based on the total mole number of all carboxylic acids, carboxylic acid anhydrides and carboxylic acid lower alkyl esters is preferably 0.1 to 10, further preferably 0.1 to 5, and particularly preferably 0.1 to 2. If the use amount falls within the range, e.g., further satisfactory adhesive strength is obtained.

Preferable examples of polyester polyol (B1-2) include a polyester diol between an ethylene oxide adduct to diol (e.g., an ethylene oxide adduct to ethylene glycol, an ethylene oxide adduct to propylene glycol) and a dicarboxylic acid (e.g., adipic acid, sebacic acid, maleic acid and phthalic acid), a dicarboxylic acid anhydride and/or a dicarboxylic acid lower alkyl ester (e.g., dicarboxylic acid methyl or ethyl ester); and a polyester diol between a co-adduct of ethylene oxide and an alkylene oxide having 3 to 8 carbon atoms to a diol (e.g., a random or block co-adduct of ethylene oxide and 1,2- or 1,3-propylene oxide to ethylene glycol, and a random or block co-adduct of ethylene oxide and 1,4-butylene oxide to propylene glycol) and a dicarboxylic acid, a dicarboxylic acid anhydride and/or a dicarboxylic acid lower alkyl ester.

Of them, in view of e.g., adhesive strength, a polyester diol between an ethylene oxide adduct to a diol and a dicarboxylic acid, a dicarboxylic acid anhydride and/or a dicarboxylic acid lower alkyl ester; and a polyester diol between co-adduct of ethylene oxide and propylene oxide to a diol and a dicarboxylic acid, a dicarboxylic acid anhydride and/or a dicarboxylic acid lower alkyl ester are preferable. Further preferably, a polyester diol between an ethylene oxide adduct to a diol and a dicarboxylic acid, a dicarboxylic acid anhydride and/or a dicarboxylic acid lower alkyl ester is mentioned.

A polyester polyol (B1-2) may be a single compound or a mixture of two or more compounds.

The hydroxyl-group equivalent of a polyester polyol (B1-2) is preferably 50 to 5000, further preferably 100 to 4000, and particularly preferably 200 to 3000. If the hydroxyl-group equivalent falls within the range, e.g., further satisfactory adhesive strength is obtained.

A hydrophilic polyol (B1) may be a single compound or a mixture of two or more compounds.

As the hydrophilic polyol (B1), a polyether polyol (B1-1) is preferable since the reactivity to water increases and e.g., further satisfactory adhesive strength is obtained; further preferably, an ethylene oxide adduct to a diol and a co-adduct of ethylene oxide and propylene oxide to a diol are mentioned; and particularly preferably, a co-adduct of ethylene oxide and propylene oxide to a diol is mentioned.

The content (wt %) of an oxyethylene group in a hydrophilic polyol (B1) based on the weight of the hydrophilic polyol (B1) is preferably 30 to 100, further preferably 40 to 95, and still further preferably 50 to 90. If the content falls within the range, e.g., further satisfactory adhesive strength is obtained.

Examples of other polyols (B2) having low hydrophilicity include diols and polyols of 3 to 6 valences as described in the above section of a compound having at least two active hydrogen atoms. Other than these, a polyol containing an oxyalkylene group and having an oxyethylene group content of less than 30 wt % based on the weight of the polyol (B2), is included. For example, a polyether polyol (B2-1), a polyester polyol (B2-2) obtain from the polyether polyol (B2-1) as an essential ingredient, and a polyester polyol (B2-3) containing neither an oxyethylene group nor an oxyalkylene group having 3 to 8 carbon atoms, can be used.

As the polyether polyol (B2-1), e.g., a (co)-adduct of an alkylene oxide having 3 to 8 carbon atoms to a compound having at least two active hydrogen atoms and a co-adduct of ethylene oxide and an alkylene oxide having 3 to 8 carbon atoms to a compound having at least two active hydrogen atoms can be used. However, the oxyethylene group content based on the weight of the polyol (B2-1) is less than 30 wt %.

Preferable examples of the polyether polyol (B2-1) include a polypropylene glycol (a 1,2- or 1,3-propylene oxide adduct to propylene glycol), an ethylene oxide adduct to a polyalkylene glycol (e.g., a block adduct of ethylene oxide and propylene oxide to ethylene glycol or propylene glycol and having an ethylene oxide content of 5 to 30 wt %), a random copolymer of propylene oxide and ethylene oxide (e.g., a random adduct of ethylene oxide and propylene oxide to ethylene glycol or propylene glycol and having an ethylene oxide content of 10 to 25 wt %), a polytetramethylene glycol (a 1,2-, 1,3-, 2,3- or 1,4-butylene oxide adduct to 1,4-butylene glycol), and a copolymer of 1,4-butylene oxide and ethylene oxide (a block or random adduct of ethylene oxide (10 to 25 wt %) and 1,4-butylene oxide (75 to 90 wt %) to ethylene glycol or butylene glycol and having an ethylene oxide content of 10 to 25 wt %).

Of these, in view of e.g., adhesiveness, an ethylene oxide adduct (ethylene oxide content: 5 to 30 wt %) to a polypropylene glycol is preferable, and an ethylene oxide adduct to polypropylene glycol (ethylene oxide content: 15 to 30 wt %) is further preferable.

A polyether polyol (B2-1) may be a single compound or a mixture of two or more compounds.

The preferable range of hydroxyl-group equivalent of a polyether polyol (B2-1) is the same as the range in the case of a polyether polyol (B1-1).

As the polyester polyol (B2-2) obtained from a polyether polyol (B2-1) as an essential ingredient, e.g., a polyester polyol that can be derived from a polyether polyol (B2-1) and a dicarboxylic acid, a dicarboxylic acid anhydride or a dicarboxylic acid lower alkyl ester as mentioned above can be used.

Preferable examples of the polyester polyol (B2-2) include a polyester polyol which can be derived from a polypropylene glycol (1,2- or 1,3-propylene oxide adduct to a propylene glycol), an ethylene oxide adduct to a polyalkylene glycol (e.g., a block adduct of ethylene oxide and propylene oxide to ethylene glycol or propylene glycol and having an ethylene oxide content of 5 to 30 wt %), a random copolymer of propylene oxide and ethylene oxide (e.g., a random adduct of ethylene oxide and propylene oxide to ethylene glycol or propylene glycol and having an ethylene oxide content of 10 to 25 wt %), a polytetramethylene glycol (1,2-, 1,3-, 2,3- or 1,4-butylene oxide adduct to 1,4-butylene glycol), and/or a copolymer of 1,4-butylene oxide and ethylene oxide (e.g., block or random adduct of ethylene oxide (10 to 25 wt %) and 1,4-butylene oxide (75 to 90 wt %) to ethylene glycol or butylene glycol and having an ethylene oxide content of 10 to 25 wt %), and a dicarboxylic acid (e.g., adipic acid, sebacic acid, maleic acid and phthalic acid), a dicarboxylic acid anhydride and/or a dicarboxylic acid lower alkyl ester (e.g., a methyl ester and ethyl ester of dicarboxylic acid).

A polyester polyol (B2-2) may be a single compound or a mixture of two or more compounds.

As a polyester polyol (B2-3) containing neither an oxyethylene group nor an oxyalkylene group having 3 to 8 carbon atoms, for example, a polyester that can be derived from at least one of the above diols and the above polyols of 3 to 6 valences, and at least one of the above dicarboxylic acids, the above dicarboxylic acid anhydrides and the above dicarboxylic acid lower alkyl esters, and a polyester derived from ring-opening polymerization of a caprolactone can be used.

Preferable examples of the polyester polyol (B2-3) include a polyester diol derived from butane diol and adipic acid; a polyester diol derived from ethylene glycol and adipic acid; a polyester diol derived from hexamethylene glycol and adipic acid; a polyester diol derived from ethylene glycol and butane diol, and adipic acid; a polyester diol derived from ethylene glycol and sebacic acid; a polyester diol derived from cyclohexane diol and phthalic acid; and a polycaprolactone derived from ring-opening polymerization of a caprolactone.

A polyester polyol (B2-3) may be a single compound or a mixture of two or more compounds.

Of these other polyols (B2) having low hydrophilicity, a polyether polyol (B2-1) having an oxyethylene group content of less than 30 wt % is preferable, in view of e.g., adhesive strength; further preferably, polypropylene glycol and an ethylene oxide (5 to 15 wt %) adduct to polypropylene glycol are mentioned; and particularly preferably polypropylene glycol is mentioned.

The content (wt %) of an oxyethylene group in the whole polyol component (B) based on the weight of the polyol component (B) is preferably 30 to 100, further preferably 35 to 98, particularly preferably 40 to 95 and most preferably 50 to 90. If the content falls within the range, e.g., further satisfactory adhesive strength is obtained.

Furthermore, the average hydroxyl-group equivalent of the whole polyol component (B) is preferably 50 to 5000, further preferably 100 to 4000, and particularly preferably 200 to 3000. If the equivalent falls within the range, e.g., further satisfactory adhesive strength is obtained.

When a hydrophilic polyol (B1) and another polyol (B2) having low hydrophilicity are used in combination, as the hydrophilic polyol (B1), a polyether polyol (B1-1) is preferable; an ethylene oxide adduct to a diol (e.g., an ethylene oxide adduct to ethylene glycol and an ethylene oxide adduct to propylene glycol) and a co-adduct of ethylene oxide and an alkylene oxide having 3 to 8 carbon atoms to a diol (e.g., a random or block co-adduct of ethylene oxide and propylene oxide to ethylene glycol, and a random or block co-adduct of ethylene oxide and butylene oxide to ethylene glycol) are further preferable; a co-adduct of ethylene oxide and propylene oxide to a diol is still further preferable; and a random co-adduct of ethylene oxide and propylene oxide to a diol is particularly preferable.

When (B1) and (B2) are used in combination, as the other polyols (B2) having low hydrophilicity, other than a diol and a polyol of 3 to 6 valences, a polyether polyol having an oxyethylene group content of less than 30 wt % based on the weight of the polyol (B2) is preferable; a polyether polyol containing an oxypropylene group and having an oxyethylene group content of less than 30 wt % based on the weight of the polyol (B2) is further preferable; and a polypropylene glycol is particularly preferable.

When (B1) and (B2) are used in combination, as the polyol component (B), in view of adhesiveness, a mixture of a polyether polyol (B1-1) and a polyether polyol having an oxyethylene group content of less than 30 wt % based on the weight of (B2) is preferable; and a mixture of a co-adduct of ethylene oxide and propylene oxide to a diol and a polyether polyol containing an oxypropylene group and having an oxyethylene group content of less than 30 wt % based on the weight of (B2) is further preferable; and a mixture of a random co-adduct of ethylene oxide and propylene oxide to a diol and polypropylene glycol is still further preferable.

When (B1) and (B2) are used in combination, the content (wt %) of (B1) in the polyol component (B) based on the weight of (B) is preferably 20 to 99 and further preferably 30 to 95, in view of adhesiveness.

The content (wt %) of (B2) in the polyol component (B) based on the weight of (B) is preferably 1 to 80 and further preferably 5 to 70, in view of adhesiveness.

The content (wt %) of an oxyethylene group in a medical adhesive based on the weight of a hydrophilic urethane prepolymer (UP) is preferably 30 to 90 and further preferably 40 to 80, in view of reactivity.

A hydrophilic urethane prepolymer (UP) is obtained by reacting a polyisocyanate component (A) and a polyol component (B).

The use amount ratio of a polyisocyanate component (A) to a polyol component (B) is preferably 1.5 to 3, further preferably 1.8 to 2.3, and particularly preferably 1.9 to 2.1 in terms of equivalent ratio (NCO group/OH group) of an isocyanate group of (A) to a hydroxyl group of (B). If the use amount ratio falls within the range, viscosity is relatively low, with the result that the adhesive can be further easily handled and further satisfactory wet adhesive strength is obtained.

As a method for producing a hydrophilic urethane prepolymer (UP), a method conventionally known in the art (e.g., International Publication No. WO03/051952) is sufficient. For example, a method of reacting a polyisocyanate component (A) and a polyol component (B) at 50 to 100° C. for 1 to 10 hours is mentioned. In this case, a polyisocyanate component (A) and a polyol component (B) may be added in the beginning or gradually added dropwise.

The hydrophilic urethane prepolymer (UP) has a structure having at least two (preferably two) isocyanate groups in a molecule without an active hydrogen atom.

Note that the isocyanate group in a hydrophilic urethane prepolymer (UP) is preferably present at a position rarely undergoing sterical hindrance, in view of e.g., the reactivity with e.g., blood and body fluid, and further preferably at a terminal position thereof rarely undergoing sterical hindrance.

Furthermore, the content (wt %) of an isocyanate group in a hydrophilic urethane prepolymer (UP) {the weight ratio of an isocyanate group to the whole weight of (UP)} is preferably 1 to 10, further preferably 1.2 to 8, and particularly preferably 1.5 to 6. If the content falls within the range, further satisfactory wet adhesive strength is obtained.

Note that the isocyanate group content can be measured by a method which includes adding an excessive amount of di-n-butylamine solution to a sample for reaction, and performing residual titration of unreacted di-n-butylamine with a hydrochloric acid standard solution in accordance with, for example, JISK7301-1995, 6.3 (isocyanate group content rate).

The number average molecular weight (Mn) of a hydrophilic urethane prepolymer (UP) is preferably 500 to 30,000, further preferably 800 to 20,000, particularly preferably 1,000 to 10,000, and most preferably 1,200 to 8,000. If Mn falls within the range, further satisfactory wet adhesive strength is obtained.

Note that the number average molecular weight (Mn) is determined by gel permeation chromatography (GPC) using polyoxyethylene glycol as a standard substance.
Apparatus: gel permeation chromatography
Solvent: THF
Reference substance: Polystyrene
Sample concentration: 0.25 wt %
Column stationary phase: TSKgelSuperH4000
Column temperature: 40° C.

In the medical adhesive of the present invention, the chlorine content in a chlorine-containing organic compound based on the weight of a hydrophilic urethane prepolymer (UP) is 0.005 wt % or less, preferably 0.004 wt % or less, and further preferably 0.003 wt % or less. The lower-limit value of the chlorine content in a chlorine-containing organic compound of a medical adhesive based on the weight of a hydrophilic urethane prepolymer (UP) is not particularly limited, but may be 0.0001 wt %. Alternatively chlorine contained in a chlorine-containing organic compound may not be contained in a medical adhesive.

If the chlorine content in a chlorine-containing organic compound falls within the range, a safe medical adhesive which can become a cured body can be provided. The cured body is hard to be degraded and decomposed and thus stable and generates less amount of carboxylic acid, aldehyde, etc. due to degradation/decomposition.

The chlorine-containing organic compound refers to an intermediate and a by-product having chlorine atoms in the molecule of organic compound, which are produced in producing a fluorine-containing non-aromatic polyisocyanate compound (A1). The chlorine-containing organic compound also refers to a reaction product between these and a polyol component (B); and more specifically, refers to the following compounds (1) to (14), a reaction product between a compound (1) and (B), a reaction product between a compound (2) and, (B), a reaction product between a compound (7) and (B), and a reaction product between a compound (8) and (B). However, the timing of adding a chlorine-containing organic compound is not limited to a step of producing an isocyanate. If it is added to a final product, the stability of a cured body will be damaged.

Compound (1): Compound represented by the following general formula (I). In the general formula (I), n represents an integer of 1 to 20.

$$OCNCH_2(CF_2)_nCH_2OCOCl \quad (I)$$

Compound (2): Compound represented by the following general formula (II). In the general formula (II), n represents an integer of 1 to 20.

$$OCNCH_2(CF_2)_nCH_2Cl \quad (II)$$

Compound (3): Compound represented by the following general formula (III). In the general formula (III), n represents an integer of 1 to 20.

$$ClOCOCH_2(CF_2)_nCH_2OCOCl \qquad (III)$$

Compound (4): Compound represented by the following general formula (IV). In the general formula (IV), n represents an integer of 1 to 22.

$$ClCH_2(CF_2)_2CH_2Cl \qquad (IV)$$

Compound (5): Compound represented by the following general formula (V).

$$O(CH_2CH_2Cl)_2 \qquad (V)$$

Compound (6): Compound represented by the following general formula (VI).

$$ClOCO(CH_2CH_2OCH_2)_2OCH_3 \qquad (VI)$$

Compound (7): Compound represented by the following general formula (VII). In the general formula (VII), n represents an integer of 1 to 22.

$$OCN(CF_2)_nOCOCl \qquad (VII)$$

Compound (8): Compound represented by the following general formula (VIII). In the general formula (VIII), n represents an integer of 1 to 22.

$$OCN(CF_2)_nCl \qquad (VIII)$$

Compound (9): Compound represented by the following general formula (IX). In the general formula (IX), n represents an integer of 1 to 22.

$$ClOCO(CF_2)_nOCOCl \qquad (IX)$$

Compound (10): Compound represented by the following general formula (X). In the general formula (X), n represents an integer of 1 to 22.

$$Cl(CF_2)_nCl \qquad (X)$$

Compound (11): Compound represented by the following general formula (XI).

$$O(CH_2CH_2OCOCl)_2 \qquad (XI)$$

Compound (12): Compound represented by the following general formula (XII).

$$ClOCOCH_2CH_2OCH_2CH_2OCOCl \qquad (XII)$$

Compound (13): Compound represented by the following general formula (XIII).

$$ClCH_2CH_2OCH_2CH_2OCOCl \qquad (XIII)$$

Compound (14): Compound represented by the following general formula (XIV).

$$ClCH_2CH_2OCH_2CH_2OCH_3 \qquad (XIV)$$

Of the above compounds (1) to (14), the compounds (1) to (4) and (7) to (10) are intermediates and by-products (C1) obtained in producing a fluorine-containing non-aromatic polyisocyanate compound (A1). Furthermore, the compounds (5), (6) and compounds (11) to (14) are chlorinated by-products (C2) which is a chlorinated solvent used in synthesizing a fluorine-containing non-aromatic polyisocyanate compound (A1). Furthermore, a reaction product between compounds (1) and (B), a reaction product between compounds (2) and (B), a reaction product between compounds (7) and (B) and a reaction product between compounds (8) and (B) are reaction products (C3) produced by a reaction with a polyol component (B).

In the above compounds (1) to (4) and (7) to (10), n is basically the same as the number of perfluoroalkylene groups of a fluorine-containing non-aromatic polyisocyanate compound (A1) which is a main product.

However, in the case where a raw material or an intermediate different in number of perfluoroalkylene groups is mixed, there is a possibility of producing a chlorine-containing organic compound derived from it. In this case, the resultant medical adhesive may contain a chlorine-containing organic compound in which n is the same as the number of perfluoroalkylene groups of a main product (A1) and a chlorine-containing organic compound in which n is different from the number of perfluoroalkylene groups of (A1).

In the medical adhesive of the present invention, the chlorine content in a chlorine-containing organic compound of the adhesive based on the weight of a hydrophilic urethane prepolymer (UP) is sufficiently 0.005 wt % or less, preferably 0.004 wt % or less and further preferably 0.003 wt % or less, in view of reducing degradation/decomposition of a cured body and generation of e.g., carboxylic acid and aldehyde due to degradation/decomposition.

In the medical adhesive, the chlorine content in a chlorine-containing organic compound can be controlled so as to fall within the above range by reducing the content of the chlorine-containing organic compound. As a reduction method, e.g., purification of a fluorine-containing non-aromatic polyisocyanate compound (A1) by distillation and a method of synthesizing a fluorine-containing non-aromatic polyisocyanate compound (A1) by a synthesis method in absence of phosgene, diphosgene and triphosgene, are mentioned.

The content of the chlorine-containing organic compound is measured by gas chromatography (GC). The conditions of GC are shown below.

<GC Conditions>
Apparatus: Gas Chromatograph GC-2014 manufactured by Shimadzu Corporation
Column: DB-5 (length: 30 m, inner diameter: 0.32 mm, film thickness: 0.25 μm) manufactured by Agilent Technologies
Temperature of vaporizing chamber: 200° C.
Detector temperature: 200° C.
Initial temperature of column: 50° C.
Column temperature raising rate: 10° C./minute
Final column temperature: 250° C.
Sample concentration: Undiluted solution is used as a measurement sample.

Note that the peak position (retention time) of each chlorine-containing organic compound is checked in advance by use of a gas chromatography mass spectrometer (GCMS).
<GCMS Conditions>
Apparatus: Quadrupole type mass spectrometer (GCMSQP-5000) manufactured by Shimadzu Corporation
<GC conditions>: The same as the above GC conditions
<MS Conditions>
Mass range in the beginning of measurement: EI35 to 600
Scan interval (I): 1.0 sec
Threshold value (T): 500
Solvent Elution time: 0.05 min
Measurement initiation time: 0.1 min
Measurement termination time: 30 min
Scan gain: 0.8 KV
<Calculation of the Chlorine Content in Chlorine-Containing Organic Compound of Medical Adhesive>

As is shown in the following formula 1, a quantitative value (g) of each of the chlorine-containing organic compounds is multiplied by the chlorine content rate of the chlorine-containing organic compound. The sum of them is divided by the weight (g) of the measurement sample to calculate obtain the chlorine content (wt %) in chlorine-containing organic compounds of a medical adhesive.

The weight of the measurement sample means the weight of a hydrophilic urethane prepolymer (UP) in the medical adhesive. For example, when the weight of a medical adhesive is 100 g, and 90 g of a hydrophilic urethane prepolymer (UP) is contained in the medical adhesive (100 g), the weight of the measurement sample is regarded as 90 g.

Chlorine content in chlorine-containing organic compounds of medical adhesive (wt %)=[{Σ(quantitative value of each of a chlorine-containing organic compounds (g)×chlorine content rate of each of the chlorine-containing organic compounds)}/weight of measurement sample (g)]× 100   (Formula 1)

Note that the chlorine content rate of each of the chlorine-containing organic compounds is calculated in accordance with the following formula.

The chlorine content rate of a chlorine-containing organic compound=the number of chlorine atoms in the chlorine-containing organic compound×the atomic weight (35.5 [g/mol]) of chlorine/molecular weight [g/mol] of the chlorine-containing organic compound   (Formula 2)

The medical adhesive of the present invention may further contain a phenolic radical scavenger (PRS). If (PRS) is contained, a sheet-form or a sponge-form cured body produced by the reaction of a hydrophilic urethane prepolymer (UP) with water can be suppressed from degradation/decomposition with time. In this manner, adhesive strength can be prevented from reducing.

Examples of the phenolic radical scavenger (PRS) include radical scavengers based on a monophenol, a bisphenol or a polymer phenol.

Examples of the monophenol-based radical scavenger include 2,6-di-t-butyl-p-cresol {for example, Antage BHT manufactured by Kawaguchi Chemical Industry Co., Ltd.}, a butylated hydroxy anisole {for example, Orient BHT manufactured by Orient Chemical Industries Co., Ltd.}, 2,6-di-t-butyl-4-ethylphenol {for example, NOCLIZER-M-17 manufactured by OUCHI SHINKO CHEMICAL INDUSTRIAL CO., LTD} and Stearyl-β-(3,5-di-t-butyl-4-hydroxyphenyl) propionate {for example, Adekastab AO-50 manufactured by Asahi Denka Co., Ltd.}.

Examples of the bisphenol-based radical scavenger include 2,2'-methylenebis(4-methyl-6-t-butylphenol) {for example, Antage W-400 manufactured by Kawaguchi Chemical Industry Co., Ltd.}, 2,2'-methylenebis(4-ethyl-6-t-butylphenol) {for example, Antage W-500 manufactured by Kawaguchi Chemical Industry Co., Ltd.}, 4,4'-butylidenebis(3-methyl-6-t-butylphenol) {for example, Antage Crystal manufactured by Kawaguchi Chemical Industry Co., Ltd.}, 4,4'-thiobis(3-methyl-6-t-butylphenol) {for example, Antage W-300, manufactured by Kawaguchi Chemical Industry Co., Ltd.}, 1,6-hexanediol-bis[3-(3,5-di-t-butyl-4-hydroxyphenyl)propionate] {for example, IRGANOX s259 manufactured by Ciba Speciality Chemicals) and 3,9-bis[1,1-dimethyl-2-[β-(3-t-butyl-4-hydroxy-5-methylphenyl)propionyl]ethyl]2,4,8,10-tetraoxaspiro[5,5]undecane {for example, Adekastab AO-80 manufactured by Asahi Denka Co., Ltd.}.

Examples of the polymer-based phenolic radical scavenger include tetrakis-[methylene-3-(3',5'-di-t-butyl-4'-hydroxyphenyl)propionate]methane {for example, IRGANOX 1010 manufactured by Ciba Speciality Chemicals}, 1,3,5-trimethyl-2,4,6-tris(3,5-di-t-butyl-4-hydroxybenzil)benzene {for example, Adekastab AO-330 manufactured by Asahi Denka Co., Ltd.}, 1,1,3-tris(2-methyl-4-hydroxy-5-t-butylphenyl) butane {for example, Adekastab AO-30 manufactured by Asahi Denka Co., Ltd.}, bis[3,3'-bis-(4'-hydroxy-3'-t-butylphenyl)butyric acid]glycol ester {for example, anti-oxidant TMOZ manufactured by Hoechst AG} and 1,3,5-tris(3',5'-di-t-butyl-4'-hydroxybenzyl)-sec-triadine-2,4,6-(1H,3H,5H)trione {for example, Adekastab AO-20, manufactured by Asahi Denka Co., Ltd.}.

The phenolic radical scavenger (PRS) has a molecular weight of preferably 500 to 1200, further preferably 600 to 1100, and particularly preferably 700 to 1000. If the molecular weight falls within the range, a cured body is further hard to be degraded and decomposed with time.

The phenolic radical scavenger (PRS) preferably has at least two hydroxyl groups, further preferably 2 to 5 hydroxyl groups, and particularly preferably 3 to 4 hydroxyl groups. If the number of hydroxyl groups falls within the range, a cured body is even harder to be degraded and decomposed with time.

Of these phenolic radical scavengers, in view of, e.g., suppression of degradation/decomposition of a cured body with time, a bisphenol-based radical scavenger and a polymer-based phenolic radical scavenger are preferable. Further preferably, tetrakis-[methylene-3-(3',5'-di-t-butyl-4'-hydroxyphenyl)propionate]methane, 1,1,3-tris(2-methyl-4-hydroxy-5-t-butylphenyl)butane, 1,3,5-trimethyl-2,4,6-tris(3,5-di-t-butyl-4-hydroxybenzyl)benzene, 1,3,5-tris(3',5'-di-t-butyl-4'-hydroxybenzyl)-sec-triadine-2,4,6-(1H,3H,5H) trione and 1,6-hexanediol-bis[3-(3,5-di-t-butyl-4-hydroxyphenyl)propionate] are mentioned.

Note that even in the same radical scavengers, a phenolic radical scavenger (PRS) is preferable than the radical scavengers other than the phenolic radical scavenger [such as an aromatic amine radical scavenger {e.g., octylated diphenylamine, N-n-butyl-p-aminophenol and phenothiazine}, a sulfur radical scavenger {e.g., dilauryl-3,3'-thiodipropionate, distearyl-3,3'-thiodipropionate and pentaerythritol tetrakis (3-laurylthiopropionate)} and a phosphoric radical scavenger {e.g., trisnonylphenyl phosphite, tris(2,4-di-t-butylphenyl) phosphite and distearylpentaerythritol diphosphite}]. If a phenolic radical scavenger (PRS) is used, degradation/decomposition of a cured body of a hydrophilic urethane prepolymer (UP) with time is suppressed and excellent adhesiveness retaining property can be shown.

Note that a phenolic radical scavenger (PRS) and a radical scavenger other than (PRS) may be used in combination.

The content (wt %) of each of these phenolic radical scavengers (PRS) based on the weight of a hydrophilic urethane prepolymer (UP) is preferably 0.01 to 3, further preferably 0.02 to 1, and particularly preferably 0.05 to 0.5. If the content falls within the range, degradation of a cured body with time can be suppressed and no harmful effect is exerted on a human body.

A phenolic radical scavenger (PRS) may be added to a hydrophilic urethane prepolymer (UP) or previously added to a polyisocyanate component (A) and/or polyol component (B) and then a hydrophilic urethane prepolymer (UP) is prepared.

The medical adhesive of the present invention may contain, if necessary, components other than a hydrophilic urethane prepolymer (UP) and a phenolic radical scavenger (PRS).

Examples of other components include a medicinal agent having a physiological activity (e.g., medicine for central nerve, medicine for allergy, medicine for a circulatory organ, medicine for a respiratory organ, medicine for a digestive organ, a hormonal agent, a metabolic agent, an antineoplastic agent, an antibiotic agent and chemotherapeutic agent), a filler (e.g., carbon black, Bengal red, calcium silicate, sodium silicate, titanium oxide, acrylic resin powder and various ceramic powders) and a plasticizer (e.g., DBP, DOP, TCP, tributoxyethyl phosphate and other esters). In the case where other components are contained, the contents of the components are appropriately determined depending upon uses or the like. Furthermore, other components may be previously added to a polyisocyanate component (A), a polyol component (B) and/or a phenolic radical scavenger (PRS) and then subjected to a prepolymerization reaction or may be added to a hydrophilic urethane prepolymer (UP) after completion of the reaction and/or a phenolic radical scavenger (PRS).

In the hydrophilic urethane prepolymer (UP) contained in the adhesive of the present invention, an isocyanate group is reacted with water (e.g., water in a body fluid such as blood and lymph fluid) to produce an amino group and carbon dioxide, and the amino group further reacts with the isocyanate group, with the result that polymerization proceeds. Carbon dioxide generated at this time contributes to spongy form to produce a coating film containing foams having wet adhesive strength and flexibility.

Accordingly, the adhesive of the present invention, when it comes into contact with a body fluid such as blood in a medical action such as a surgical operation, is rapidly polymerized with the help of a water content of the body fluid to show adhesive strength. Furthermore, initial adhesive strength can be enhanced by, if necessary, supplying water by spraying e.g., a physiological saline solution.

When body tissues are bonded by the adhesive of the present invention in a surgical operation, examples of the bonding method include a direct adhesion method in which the adhesive of the present invention is directly applied to an incision site; and a transfer adhesion method in which the adhesive is applied to a film having high release properties, such as a silicone film and a fluorine film, and an incision site is covered with the film and the film is removed after completion of the reaction.

In view of safety and adhesive strength to a living body, the medical adhesive of the present invention is preferably used for adhesion of body tissues, further preferably, lung, artery, heart, vein, trachea, esophagus, stomach, duodenum, small intestine, large intestine, rectum, liver, spleen, kidney, pancreas and nerve, still further preferably, lung, artery and heart, and particularly preferably artery.

EXAMPLES

The present invention will be more specifically described by way of Examples below; however, the present invention is not limited to these Examples alone. Note that, the term "part(s)" represents part(s) by weight and the symbol "%" represents "wt %".

Production Example 1

In accordance with the description of reference document 1 (JP 57-108055A), a fluorine-containing non-aromatic polyisocyanate {bis(isocyanatomethyl)perfluorobutane [OCN—$CH_2$—$(CF_2)_4$—$CH_2$—NCO]} (a1-1) was synthesized. The chlorine content in a chlorine-containing organic compound in (a1-1) was 0.027% and the hydrolytic chlorine content was 0.120%.

Production Example 2

The compound (a1-1) obtained in Production Example 1 was subjected to distillation under reduced pressure (75 to 80° C./3 to 5 mmHg). The resultant distillate was further subjected to distillation under reduced pressure in the same conditions. This process was repeated three times to obtain a fluorine-containing non-aromatic polyisocyanate (a1-2).

The chlorine content in a chlorine-containing organic compound in the fluorine-containing non-aromatic polyisocyanate (a1-2) was 0.012% and the hydrolytic chlorine content was 0.025%.

Production Example 3

The compound (a1-1) of Production Example 1 was mixed with methylene chloride and ion-exchanged water in a ratio of (a1-1)/methylene chloride/ion-exchanged water=10 parts/10 parts/10 parts. The mixture was washed and extracted with water five times by use of a separatory funnel for 30 seconds while shaking to separate a methylene chloride (organic) layer containing (a1-1) and a water layer. Furthermore, the organic layer containing (a1-1) was washed and extracted five times with ion-exchanged water (10 parts).

To the organic layer, 0.2 parts of anhydrous magnesium sulfate was added. The mixture was allowed to stand still, filtrated and dewatered (dried).

After methylene chloride was distilled away from the organic layer under reduced pressure at 30 to 50° C., distillation under reduced pressure (72 to 83° C./3 to 5 mmHg) was further performed to obtain a fluorine-containing non-aromatic polyisocyanate (a1-3).

The chlorine content in a chlorine-containing organic compound in the fluorine-containing non-aromatic polyisocyanate (a1-3) was 0.020%, and the hydrolytic chlorine content was 0.025%.

Production Example 4

In accordance with the description of reference document 1, a fluorine-containing non-aromatic polyisocyanate {bis(isocyanatomethyl)perfluorohexane [OCN—$CH_2$—$(CF_2)_6$—$CH_2$—NCO]} (a2-1) was synthesized. The chlorine content in a chlorine-containing organic compound in (a2-1) was 0.018% and the hydrolytic chlorine content was 0.08%.

Production Example 5

The compound (a2-1) was subjected to distillation under reduced pressure three times in the same conditions as in Production Example 2 to obtain a fluorine-containing non-aromatic polyisocyanate (a2-2). The chlorine content in a chlorine-containing organic compound in the fluorine-containing non-aromatic polyisocyanate (a2-2) was 0.011% and the hydrolytic chlorine content was 0.042%.

Production Example 6

In accordance with the description of reference document 2 (J. Macromol. Sci. Phys. B1, 831 1967), a fluorine-containing non-aromatic polyisocyanate {perfluorotrimethylene diisocyanate [OCN—$(CF_2)_3$—NCO]} (a3-1) was synthesized. The chlorine content in a chlorine-containing organic compound in (a3-1) was 0.052% and the hydrolytic chlorine content was 0.140%.

Production Example 7

The compound (a3-1) obtained in Production Example 6 was subjected to distillation under reduced pressure (55 to 60° C./300 to 360 mmHg) and further distillation under reduced pressure was repeated three times to obtain a fluorine-containing non-aromatic polyisocyanate (a3-2). The chlorine content in a chlorine-containing organic compound in the fluorine-containing non-aromatic polyisocyanate (a3-2) was 0.002% and the hydrolytic chlorine content was 0.030%.

Production Example 8

In accordance with the description of reference document 2, a fluorine-containing non-aromatic polyisocyanate {perfluorooctyl diisocyanate [OCN—$(CF_2)_8$—NCO]} (a4-1) was synthesized. The chlorine content in a chlorine-containing organic compound in (a4-1) was 0.019% and the hydrolytic chlorine content was 0.072%.

Production Example 9

The compound (a4-1) obtained in Production Example 8 was subjected to distillation under reduced pressure (110 to 115° C./220 to 260 mmHg) and further distillation under reduced pressure was repeated three times to obtain a fluorine-containing non-aromatic polyisocyanate (a4-2). The chlorine content in a chlorine-containing organic compound in the fluorine-containing non-aromatic polyisocyanate (a4-2) was 0.011% and the hydrolytic chlorine content was 0.031%.

Production Example 10

Ethylene glycol (15.5 parts) and potassium hydroxide (3.8 parts) were placed in an autoclave. After nitrogen purge (a gaseous-phase oxygen concentration: 450 ppm) was performed, dewatering was performed at 120° C. for 60 minutes under vacuum. Subsequently, a mixture of ethylene oxide (784.5 parts) and propylene oxide (200 parts) was injected with application of pressure at 100 to 130° C. over about 10 hours and thereafter continuously reacted at 130° C. for 3 hours to obtain a liquid-state crude polyether having an oxyethylene group content of 80%.

The liquid-state crude polyether (1000 parts) was placed in an autoclave. Nitrogen purge (a gaseous-phase oxygen concentration: 450 ppm) was performed and ion-exchanged water (30 parts) was added, and then, 10 parts of synthesized magnesium silicate (sodium content: 0.2%) was added. After nitrogen purge was performed again, the mixture was stirred at 90° C. for 45 minutes at a stirring rate of 300 rpm. Subsequently, filtration was performed by use of a glass filter (GF-75: manufactured by Toyo Roshi Kaisha, Ltd.) under nitrogen atmosphere to obtain an ethylene oxide/propylene oxide random co-adduct (b1). The number average molecular weight of (b1) was 4000 and the oxyethylene group content was 80%. The number of functional groups was 2.

Production Example 11

Ethylene glycol (15.5 parts) and potassium hydroxide (3.8 parts) were placed in an autoclave. After nitrogen purge (a gaseous-phase oxygen concentration: 450 ppm) was performed, dewatering was performed at 120° C. for 60 minutes under vacuum. Subsequently, a mixture of ethylene oxide (484.5 parts) and propylene oxide (500 parts) was injected with application of pressure at 100 to 130° C. over about 10 hours and thereafter continuously reacted at 130° C. for 3 hours to obtain a liquid-state crude polyether having an oxyethylene group content of 50%.

The liquid-state crude polyether was treated with synthesized magnesium silicate in the same manner as in Production Example 10 to obtain a propylene oxide adduct (b2). The number average molecular weight of (b2) was 4000 and the oxyethylene group content was 50%. The number of functional groups was 2.

Production Example 12

Ethylene glycol (60.0 parts) and potassium hydroxide (3.8 parts) were placed in an autoclave. After nitrogen purge (a gaseous-phase oxygen concentration: 450 ppm) was performed, dewatering was performed at 120° C. for 60 minutes under vacuum. Subsequently, ethylene oxide (940.0 parts) was injected with application of pressure at 100 to 130° C. over about 10 hours and thereafter continuously reacted at 130° C. for 3 hours to obtain a liquid-state crude polyether having an oxyethylene group content of 100%.

The liquid-state crude polyether was treated with synthesized magnesium silicate in the same manner as in Production Example 10 to obtain a propylene oxide adduct (b3). The number average molecular weight of (b3) was 1000 and the oxyethylene group content was 100%. The number of functional groups was 2.

Production Example 13

Ethylene glycol (30.8 parts) and potassium hydroxide (3.8 parts) were placed in an autoclave. After nitrogen purge (a gaseous-phase oxygen concentration: 450 ppm) was performed, dewatering was performed at 120° C. for 60 minutes under vacuum. Subsequently, a mixture of ethylene oxide (754.6 parts) and propylene oxide (218.8 parts) was injected with application of pressure at 100 to 130° C. over about 10 hours and thereafter continuously reacted at 130° C. for 3 hours to obtain a liquid-state crude polyether having an oxyethylene group content of 100%.

The liquid-state crude polyether was treated with synthesized magnesium silicate in the same manner as in Production Example 10 to obtain a propylene oxide adduct (b4). The number average molecular weight of (b4) was 3000 and the oxyethylene group content was 75%. The number of functional groups was 3.

Production Example 14

Propylene glycol (362 parts) and potassium hydroxide (3.8 parts) were placed in an autoclave. After nitrogen purge (a gaseous-phase oxygen concentration: 450 ppm) was performed, dewatering was performed at 120° C. for 60 minutes under vacuum. Subsequently, propylene oxide (632 parts) was injected with application of pressure at 100 to 130° C. over about 10 hours and thereafter continuously reacted at 130° C. until a volatile matter content reached 0.1% or less to obtain a liquid-state crude polyether.

The liquid-state crude polyether was treated with synthesized magnesium silicate in the same manner as in Production Example 10 to obtain a propylene oxide adduct (b5). The number average molecular weight of (b5) was 210 and the oxyethylene group content was 0%. The number of functional groups was 2.

Example 1

As a polyol component (B), a mixture of ethylene oxide/propylene oxide random co-adduct (b1) (90 parts) obtained in Production Example 10 and a propylene oxide adduct (b5) (10 parts) obtained in Production Example 14 was used and dewatered under reduced pressure at 100° C. for 2 hours under a nitrogen atmosphere and then cooled to 40° C. To this, the compound (a1-2) (45.6 parts (NCO group/OH group ratio=2/1), which was obtained as a polyisocyanate component (A) in Production Example 2, was added. The mixture was uniformly stirred, raised in temperature to 80° C., and reacted at 80° C. for 6 hours to produce a hydrophilic urethane prepolymer as the medical adhesive of the present invention (P1). The hydrolytic chlorine content (%) in the polyisocyanate component (A), the oxyethylene group content (%) in the polyol component (B), the isocyanate group content (%) in the hydrophilic urethane prepolymer, the number average molecular weight (Mn) of the hydrophilic urethane prepolymer, the oxyethylene group content (%) in the hydrophilic urethane prepolymer, the chlorine content (%) in a chlorine-containing organic compound in a medical adhesive and the hydrolytic chlorine content (%) in the medical adhesive are shown in Table 1-2.

Furthermore, to 100 parts of (P1), 0.2 parts of tetrakis-[methylene-3-(3',5'-di-t-butyl-4'-hydroxyphenyl)propionate]methane (IRGANOX 1010, manufactured by Ciba Speciality Chemicals) as a phenolic radical scavenger (PRS), was added to obtain (P1-1).

Furthermore, to 100 parts of (P1), 0.5 parts of tetrakis-[methylene-3-(3',5'-di-t-butyl-4'-hydroxyphenyl)propionate]methane was added to obtain (P1-2).

Examples 2 to 13

Hydrophilic urethane prepolymers were produced as medical adhesives (P2) to (P13) by using the corresponding materials described in Table 1-1 in place of the polyisocyanate component (A) and the polyol component (B) of Example 1. The hydrolytic chlorine content (%) in a polyisocyanate component (A), the oxyethylene group content (%) in a polyol component (B), the isocyanate group content (%) in a hydrophilic urethane prepolymer, the number average molecular weight (Mn) of a hydrophilic urethane prepolymer and the oxyethylene group content (%) in a hydrophilic urethane prepolymer of each medical adhesive, the chlorine content (%) in a chlorine-containing organic compound in each medical adhesive and the hydrolytic chlorine content (%) in each medical adhesive are shown in Table 1-2.

Furthermore, (P2-1) to (P13-1) and (P2-2) to (P13-2) were obtained in the same manner as in Example 1 except that (P2) to (P13) were separately used in place of (P1).

Comparative Examples 1 to 14

Hydrophilic urethane prepolymers were produced as medical adhesives (P'1) to (P'14) by using the corresponding materials described in Table 2-1 in place of the polyisocyanate component (A) and the polyol component (B) of Example 1. The hydrolytic chlorine content (%) in a polyisocyanate component (A), the oxyethylene group content (%) in a polyol component (B), the isocyanate group content (%) in a hydrophilic urethane prepolymer, the number average molecular weight (Mn) of a hydrophilic urethane prepolymer and the oxyethylene group content (%) in a hydrophilic urethane prepolymer of each medical adhesive, the chlorine content (%) in a chlorine-containing organic compound in each medical adhesive and the hydrolytic chlorine content (%) in each medical adhesive are shown in Table 2-2.

Furthermore, (P'1-1) to (P'14-1) and (P'1-2) to (P'14-2) were obtained in the same manner as in Example 1 except that (P'1) to (P'14) were used in place of (P1).

TABLE 1-1

| | | | Examples | | | | | | | | | | | | |
|---|---|---|---|---|---|---|---|---|---|---|---|---|---|---|---|
| | | | 1 | 2 | 3 | 4 | 5 | 6 | 7 | 8 | 9 | 10 | 11 | 12 | 13 |
| Polyisocyanate component (A) (parts by weight) | (A1) | a1-1 | — | — | — | — | — | — | — | — | — | — | — | — | — |
| | | a1-2 | 45.6 | — | — | — | 40 | 40 | 44 | 63 | 44 | — | — | 63 | — |
| | | a1-3 | — | — | — | — | — | — | — | — | — | — | — | — | — |
| | | a2-1 | — | — | — | — | — | — | — | — | — | — | — | — | — |
| | | a2-2 | — | 59.7 | — | — | — | — | — | — | — | — | — | — | — |
| | | a3-1 | — | — | — | — | — | — | — | — | — | — | — | — | — |
| | | a3-2 | — | — | 31 | — | — | — | — | — | — | 14 | 11 | — | 14 |
| | | a4-1 | — | — | — | — | — | — | — | — | — | — | — | — | — |
| | | a4-2 | — | — | — | 66 | — | — | — | — | — | — | — | — | — |
| | (A2) | a5 | — | — | — | — | 2.44 | — | — | — | — | — | — | — | — |
| | | a6 | — | — | — | — | — | 2.36 | — | — | — | — | — | — | — |
| | | a7 | — | — | — | — | — | — | 2.12 | — | — | — | — | — | — |
| Polyol component (B) (parts by weight) | (B1) | b1 | 90 | 90 | 90 | 90 | 90 | 90 | 90 | — | — | 90 | 90 | 90 | 90 |
| | | b2 | — | — | — | — | — | — | — | — | 90 | — | — | — | — |
| | | b3 | — | — | — | — | — | — | — | 90 | — | — | — | — | — |
| | | b4 | — | — | — | — | — | — | — | — | — | — | — | — | 10 |
| | (B2) | b5 | 10 | 10 | 10 | 10 | 10 | 10 | 10 | 4.74 | 10 | — | — | 10 | — |
| | | b6 | — | — | — | — | — | — | — | — | — | 4.74 | — | — | — |

TABLE 1-2

| | | Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Hydrolytic chlorine content (%) in polyisocyanate component (A) | | 0.025 | 0.042 | 0.030 | 0.031 | 0.023 | 0.023 | 0.024 | 0.025 | 0.025 | 0.030 | 0.030 | 0.025 | 0.030 |
| Oxyethylene group content (%) in polyol component (B) | | 72 | 72 | 72 | 72 | 72 | 72 | 72 | 95 | 45 | 76 | 80 | 72 | 79.5 |
| Medical adhesive | | P1 | P2 | P3 | P4 | P5 | P6 | P7 | P8 | P9 | P10 | P11 | P12 | P13 |
| Isocyanate group content (%) in hydrophilic urethane prepolymer | | 4.0 | 3.8 | 4.5 | 3.7 | 4.2 | 4.3 | 4.4 | 5.2 | 4.2 | 2.4 | 2.0 | 7.3 | 2.2 |
| Number average molecular weight (Mn) of hydrophilic urethane prepolymer | | 5200 | 5600 | 4800 | 5900 | 5300 | 5400 | 8200 | 3200 | 5500 | 6600 | 9300 | 4300 | 11000 |
| Oxyethylene group content (%) in hydrophilic urethane prepolymer | | 49.5 | 45.1 | 55.0 | 43.4 | 50.5 | 50.6 | 49.3 | 57.1 | 31.3 | 66.2 | 71.5 | 44.2 | 69.7 |
| Chlorine content (%) in chlorine-containing organic compound in medical adhesive | | 0.0038 | 0.0041 | 0.0005 | 0.0044 | 0.0034 | 0.0034 | 0.0036 | 0.0048 | 0.0037 | 0.0003 | 0.0002 | 0.0046 | 0.0002 |
| Hydrolytic chlorine content (%) in medical adhesive | | 0.008 | 0.016 | 0.007 | 0.012 | 0.007 | 0.007 | 0.008 | 0.010 | 0.008 | 0.004 | 0.003 | 0.010 | 0.004 |
| Evaluation | No addition of antioxidant | | | | | | | | | | | | | |
| | Decomposition rate (%) | 1.60 | 0.30 | 0.20 | 3.80 | 0.10 | 0.80 | 2.00 | 5.00 | 3.20 | 0.40 | 1.20 | 4.90 | 1.60 |
| | pH | 7.16 | 7.29 | 7.30 | 6.95 | 7.31 | 7.24 | 7.13 | 6.84 | 7.01 | 7.28 | 7.20 | 6.85 | 7.16 |
| | Aldehyde | 0.020 | 0.040 | 0.053 | 0.050 | 0.054 | 0.042 | 0.023 | 0.060 | 0.040 | 0.049 | 0.036 | 0.120 | 0.029 |
| | Ratio (%) of peak intensity Carboxylic acid | 0.010 | 0.000 | 0.006 | 0.040 | 0.004 | 0.020 | 0.042 | 0.090 | 0.056 | 0.011 | 0.028 | 0.080 | 0.035 |
| | Addition of antioxidant (0.2%) Medical adhesive | P1-1 | P2-1 | P3-1 | P4-1 | P5-1 | P6-1 | P7-1 | P8-1 | P9-1 | P10-1 | P11-1 | P12-1 | P13-1 |
| | Decomposition rate (%) | 0.4 | 6.1 | 0 | 0.8 | 0 | 1.3 | 2.3 | 4.5 | 2.3 | 0 | 0.4 | 0.4 | 0.2 |
| | pH | 7.28 | 6.74 | 7.32 | 7.24 | 7.32 | 7.19 | 7.10 | 6.89 | 7.10 | 7.32 | 7.28 | 7.28 | 7.30 |
| | Aldehyde | 0.049 | 0.000 | 0.056 | 0.042 | 0.056 | 0.034 | 0.019 | 0.030 | 0.019 | 0.056 | 0.049 | 0.049 | 0.053 |
| | Ratio (%) of peak intensity Carboxylic acid | 0.011 | 0.062 | 0.001 | 0.020 | 0.001 | 0.030 | 0.046 | 0.063 | 0.046 | 0.001 | 0.011 | 0.040 | 0.006 |
| | Addition of antioxidant (0.5%) Medical adhesive | P1-2 | P2-2 | P3-2 | P4-2 | P5-2 | P6-2 | P7-2 | P8-2 | P9-2 | P10-2 | P11-2 | P12-2 | P13-2 |
| | Decomposition rate (%) | 0.4 | 6.2 | 0 | 0 | 0 | 1.1 | 2.1 | 4.9 | 2.3 | 0 | 0.5 | 0.3 | 0.3 |
| | pH | 7.28 | 6.73 | 7.32 | 7.32 | 7.32 | 7.21 | 7.12 | 6.85 | 7.10 | 7.32 | 7.27 | 7.29 | 7.29 |
| | Aldehyde | 0.049 | 0.025 | 0.056 | 0.056 | 0.056 | 0.037 | 0.022 | 0.040 | 0.019 | 0.056 | 0.047 | 0.051 | 0.051 |
| | Ratio (%) of peak intensity Carboxylic acid | 0.011 | 0.062 | 0.001 | 0.001 | 0.001 | 0.026 | 0.043 | 0.064 | 0.046 | 0.001 | 0.013 | 0.030 | 0.009 |

TABLE 2-1

| | | | Comparative Examples | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| Polyisocyanate component (A) (parts by weight) | (A1) | a1-1 | 45.6 | — | — | — | — | 40 | 40 | 44 | 63 | 44 | — | — | 63 | — |
| | | a1-2 | — | — | — | — | — | — | — | — | — | — | — | — | — | — |
| | | a1-3 | — | 45.6 | — | — | — | — | — | — | — | — | — | — | — | — |
| | | a2-1 | — | — | 59.7 | — | — | — | — | — | — | — | — | — | — | — |
| | | a2-2 | — | — | — | — | — | — | — | — | — | — | — | — | — | — |
| | | a3-1 | — | — | — | 31 | — | — | — | — | — | — | 14 | 11 | — | 14 |
| | | a3-2 | — | — | — | — | — | — | — | — | — | — | — | — | — | — |
| | | a4-1 | — | — | — | — | 66 | — | — | — | — | — | — | — | — | — |
| | | a4-2 | — | — | — | — | — | — | — | — | — | — | — | — | — | — |
| | (A2) | a5 | — | — | — | — | — | 2.44 | — | — | — | — | — | — | — | — |
| | | a6 | — | — | — | — | — | — | 2.36 | — | — | — | — | — | — | — |
| | | a7 | — | — | — | — | — | — | — | 2.12 | — | — | — | — | — | — |
| Polyol component (B) (parts by weight) | (B1) | b1 | 90 | 90 | 90 | 90 | 90 | 90 | 90 | 90 | — | — | 90 | 90 | 90 | 90 |
| | | b2 | — | — | — | — | — | — | — | — | — | 90 | — | — | — | — |
| | | b3 | — | — | — | — | — | — | — | — | 90 | — | — | — | — | — |
| | | b4 | — | — | — | — | — | — | — | — | — | — | — | — | — | 10 |
| | (B2) | b5 | 10 | 10 | 10 | 10 | 10 | 10 | 10 | 10 | 4.74 | 10 | — | — | 10 | — |
| | | b6 | — | — | — | — | — | — | — | — | — | — | 4.74 | — | — | — |

TABLE 2-2

| | Comparative Examples | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Hydrolytic chlorine content (%) in polyisocyanate component (A) | 0.120 | 0.025 | 0.080 | 0.140 | 0.072 | 0.108 | 0.108 | 0.116 | 0.120 | 0.120 | 0.140 | 0.140 | 0.120 | 0.140 |
| Oxyethylene group content (%) in polyol component (B) | 72 | 72 | 72 | 72 | 72 | 72 | 72 | 72 | 95 | 45 | 76 | 80 | 72 | 79.5 |
| Medical adhesive | P'1 | P'2 | P'3 | P'4 | P'5 | P'6 | P'7 | P'8 | P'9 | P'10 | P'11 | P'12 | P'13 | P'14 |
| Isocyanate group content (%) in hydrophilic urethane prepolymer | 4.0 | 4.0 | 4.0 | 4.5 | 3.7 | 4.2 | 4.3 | 4.4 | 5.2 | 4.2 | 2.4 | 2.0 | 7.3 | 2.2 |
| Number average molecular weight (Mn) of hydrophilic urethane prepolymer | 5400 | 5400 | 5600 | 4800 | 5900 | 5400 | 5300 | 8300 | 3200 | 5500 | 6600 | 9200 | 4300 | 11000 |
| Oxyethylene group content (%) in hydrophilic urethane prepolymer | 49.5 | 49.5 | 45.1 | 55.0 | 43.4 | 50.5 | 50.6 | 49.3 | 57.1 | 31.3 | 66.2 | 71.5 | 44.2 | 69.7 |
| Chlorine content (%) in chlorine-containing organic compound in medical adhesive | 0.0085 | 0.0063 | 0.0067 | 0.0123 | 0.0076 | 0.0076 | 0.0076 | 0.0081 | 0.0108 | 0.0083 | 0.0067 | 0.0057 | 0.0104 | 0.0064 |
| Hydrolytic chlorine content (%) in medical adhesive | 0.038 | 0.008 | 0.030 | 0.033 | 0.029 | 0.034 | 0.034 | 0.036 | 0.048 | 0.037 | 0.018 | 0.015 | 0.046 | 0.017 |
| Evaluation No addition of antioxidant Decomposition rate (%) | 64.0 | 52.4 | 52.0 | 74.0 | 55.0 | 55.8 | 54.0 | 56.8 | 64.0 | 60.9 | 51.0 | 44.0 | 64.9 | 56.4 |
| pH | 1.95 | 2.34 | 2.37 | 1.32 | 2.09 | 2.01 | 2.18 | 1.91 | 1.23 | 1.52 | 2.47 | 3.13 | 1.14 | 1.95 |
| Aldehyde Ratio (%) of peak intensity | 1.58 | 1.30 | 1.28 | 2.09 | 1.48 | 1.54 | 1.41 | 1.61 | 2.17 | 1.92 | 1.21 | 0.81 | 2.25 | 1.58 |
| Carboxylic acid Ratio (%) of peak intensity | 4.09 | 2.85 | 2.76 | 6.10 | 3.63 | 3.89 | 3.32 | 4.22 | 5.82 | 5.79 | 2.50 | 1.08 | 5.20 | 4.09 |
| Addition of antioxidant (0.2%) Medical adhesive | P'1-1 | P'2-1 | P'3-1 | P'4-1 | P'5-1 | P'6-1 | P'7-1 | P'8-1 | P'9-1 | P'10-1 | P'11-1 | P'12-1 | P'13-1 | P'14-1 |
| Decomposition rate (%) | 54.0 | 58.6 | 45.2 | 67.2 | 56.0 | 59.0 | 59.2 | 51.0 | 59.0 | 58.0 | 42.3 | 41.2 | 59.9 | 58.0 |
| pH | 2.18 | 1.75 | 3.02 | 0.93 | 1.99 | 1.71 | 1.69 | 2.47 | 1.71 | 1.80 | 3.29 | 3.40 | 1.62 | 3.50 |
| Aldehyde Ratio (%) of peak intensity | 1.41 | 1.32 | 0.87 | 1.82 | 1.55 | 1.77 | 1.79 | 1.21 | 1.77 | 1.70 | 0.72 | 0.42 | 1.84 | 0.90 |
| Carboxylic acid Ratio (%) of peak intensity | 3.32 | 2.83 | 1.28 | 4.82 | 3.95 | 5.03 | 5.11 | 2.50 | 5.03 | 4.65 | 0.83 | 0.15 | 5.38 | 2.80 |
| Addition of antioxidant (0.5%) Medical adhesive | P'1-2 | P'2-2 | P'3-2 | P'4-2 | P'5-2 | P'6-2 | P'7-2 | P'8-2 | P'9-2 | P'10-2 | P'11-2 | P'12-2 | P'13-2 | P'14-2 |
| Decomposition rate (%) | 53.0 | 58.2 | 45.0 | 67.2 | 53.0 | 59.6 | 58.9 | 51.3 | 60.2 | 59.0 | 42.5 | 38.0 | 59.2 | 58.4 |
| pH | 2.28 | 1.79 | 3.04 | 0.93 | 2.28 | 1.65 | 1.71 | 2.44 | 1.59 | 1.71 | 3.27 | 3.70 | 1.69 | 3.60 |
| Aldehyde Ratio (%) of peak intensity | 1.34 | 1.41 | 0.86 | 1.79 | 1.34 | 1.82 | 1.77 | 1.23 | 1.87 | 1.77 | 0.73 | 0.91 | 1.79 | 0.92 |

TABLE 2-2-continued

| | Comparative Examples | | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Carboxylic acid Ratio (%) of peak intensity | 3.03 | 2.81 | 1.24 | 4.79 | 3.03 | 5.26 | 4.99 | 2.57 | 5.50 | 5.03 | 0.86 | 1.32 | 4.87 | 2.70 |

As the components shown in Table 1-1 and Table 2-1, the followings were used.

Polyisocyanate Components a5: Hexamethylene diisocyanate [OCN—$(CH_2)_6$—NCO], the chlorine content in a chlorine-containing organic compound is 0.000%, the hydrolytic chlorine content is 0.005%, and the product name is "Duranate 50M-HDI," manufactured by Asahi Kasei Chemicals Corporation, a6: 2,4-Tolylene diisocyanate, the chlorine content in a chlorine-containing organic compound is 0.000%, the hydrolytic chlorine content is 0.004%, and the product name is "CORONATE T-100," manufactured by Nippon Polyurethane Industry Co., Ltd., a7: Isocyanurate-form hexamethylene diisocyanate, the chlorine content in a chlorine-containing organic compound is 0.000%, the hydrolytic chlorine content is 0.004%, and the product name is "Duranate TPA-100," manufactured by Asahi Kasei Corporation.

Polyol Components b6: Polytetramethylene ether glycol 650, the number average molecular weight is 650, the oxyethylene group content is 0%, and the product name is "PTMG 650," manufactured by Mitsubishi Chemical Corporation.

<Chlorine Content in a Chlorine-Containing Organic Compound in Polyisocyanates (a1-1) to (a7)>

The chlorine content (wt %) in a chlorine-containing organic compound in each of polyisocyanates (a1-1) to (a7) was obtained by measuring the content of a chlorine-containing organic compound in each of polyisocyanates (a1-1) to (a7) used as a measurement sample by GC (the conditions are the same as defined above) and making a calculation in accordance with the following formula 3.

The chlorine content (wt %) in a chlorine-containing organic compound in a polyisocyanate component $(A)$=[{Σ(quantitative value (g) of each chlorine-containing organic compound×each chlorine content rate of a chlorine-containing organic compound)}/weight (g) of a measurement sample]×100     (Formula 3)

Note that the chlorine content rate of each chlorine-containing organic compound was calculated from formula 2 above.

<Evaluation 1: Stability of Cured Coating Film>

To a slide glass, each (0.2 to 0.3 g) of the medical adhesives (P1) to (P13) and (P'1) to (P'14) was applied. The slide glass was dipped in ultrapure water contained in a 100 mL-beaker such that the applied portion was completely dipped. In this manner, each medical adhesive was cured to prepare a cured coating film. About 2 hours later, the cured coating film was taken out.

The cured coating film was placed on a release paper and lyophilized for 12 to 36 hours. The weight (w1) of the cured coating film after the lyophilization was measured and the film was placed in a container, dipped in ultrapure water (30 mL) and stored airtight in the container.

This was placed in a dryer of 60° C. and taken out after 4 weeks. Insoluble matter and the supernatant were separated by decantation and the insoluble matter was placed on a release paper and lyophilized for 24 to 48 hours. The supernatant was poured in a Petri dish and also lyophilized for 24 to 48 hours.

The weight (w2) of the lyophilized insoluble matter was measured and the decomposition rate was calculated in accordance with the following expression.

Decomposition rate=$(w1-w2)/w1 \times 100$

The results of decomposition rates (%) of medical adhesives (P1) to (P13) and (P'1) to (P'14) are shown in Table 1-2 and Table 2-2.

<Evaluation 2: Generation of Aldehyde and Carboxylic Acid>

With respect to the supernatant obtained in Evaluation 1, pH was measured in accordance with JIS Z 8802. Furthermore, 10 mg of the lyophilized supernatant was dissolved in heavy DMSO (0.5 mL). This was subjected, as a sample, to 1H NMR measurement. The ratio (%) of the peak intensity of each of aldehyde (a peak near 9.6 ppm), carboxylic acid (a peak near 12.4 ppm) and the peak intensity of e.g., a methyl group and methine group (a peak of 1.4 to 0.6 ppm) was obtained. Based on the ratio, whether aldehyde and carboxylic acid were generated was evaluated. The results are shown in Table 1-2 and Table 2-2.

<Irradiation of γ Ray>

A polypropylene syringe (2 mL) was charged with each of medical adhesives (P1-1) to (P13-1), (P1-2) to (P13-2), (P'1-1) to (P'14-1) and (P'1-2) to (P'14-2) under a nitrogen atmosphere and irradiated with γ ray (25 kGy) to obtain irradiated medical adhesives (P1-1) to (P13-1), (P1-2) to (P13-2), (P'1-1) to (P'14-1) and (P'1-2) to (P'14-2).

Decomposition rates were measured in the same manner as in <Evaluation 1> and <Evaluation 2> except that "irradiated medical adhesives (P1-1) to (P13-1), (P1-2) to (P13-2), (P'1-1) to (P'14-1) and (P'1-2) to (P'14-2)" were used in place of the "medical adhesives (P1) to (P13) and (P'1) to (P'14)" used in Evaluations 1 and 2. The results are shown in Table 1-2 and Table 2-2.

As is apparent from the results of Table 2-2, in adhesives of Comparative Examples 1 to 14 (the chlorine content in a chlorine-containing organic compound in a medical adhesive is larger than 0.005% (0.0057 to 0.0123%)), it is found that decomposition of a cured coating film is accelerated and aldehyde and carboxylic acid are generated. When a cured coating film is decomposed, adhesive strength reduces, with the result that the medical adhesive cannot prevent effusion of body fluid such as blood, gas from the lung, and the content of the digestive organ, for example.

Furthermore, in the medical adhesives of Comparative Examples 1 to 14 having a large chlorine content in a chlorine-containing organic compound, even if an antioxidant was added, degradation/decomposition in a sterilization treatment with γ-ray irradiation was not successfully prevented. Furthermore, even if the addition amount of antioxidant was increased, degradation/decomposition was not successfully suppressed.

On the other hand, from the results shown in Table 1-2, it is found that the adhesives of Examples 1 to 13 containing chlorine in a content of 0.005% or less (0.0005 to 0.0048%) in a chlorine-containing organic compound is rarely decomposed. Therefore, a tissue can be sealed for a long time. Furthermore, it is also found that since toxic aldehyde and carboxylic acid are rarely produced, the adhesives are safe.

Furthermore, if each of medical adhesives of Examples 1 to 13 of the present invention having a low chlorine content in a chlorine-containing organic compound is used in combination with an antioxidant, it is found that a highly stable medical adhesive (a cured body of which is hard to be degraded and decomposed even after sterilization treatment with γ-ray irradiation required for a medical adhesive) can be provided.

INDUSTRIAL APPLICABILITY

The medical adhesive of the present invention, since it has extremely excellent wet adhesive strength even after sterilization treatment with γ-ray irradiation, can be particularly effectively used for adhesion of a movable body tissue, and not only works extremely effectively as a medical adhesive for, e.g., adhesion of the lung, artery, heart, vein, trachea, esophagus, stomach, duodenum, small intestine, large intestine, rectum, liver, spleen, kidney, pancreas, nerve and the like, inhibiting blood leakage, inhibiting enzyme leakage from the digestive organ, temporary fixation before suture and reinforcement of a diseased part, but also shows high reliability and high performance in joining of e.g., a wound area and an incision site and in dental bonding treatment. The medical adhesive of the present invention particularly shows extremely high reliability and high performance in bonding a movable tissue such as lung, artery and heart.

The invention claimed is:

1. A medical adhesive comprising a hydrophilic urethane prepolymer (UP) obtained by reacting a polyisocyanate component (A) comprising a fluorine-containing non-aromatic polyisocyanate compound (A1) as an essential ingredient and a polyol component (B) comprising a hydrophilic polyol (B1) as an essential ingredient,
   wherein a chlorine content derived from a chlorine-containing organic compound is 0.0002 wt % or more and 0.005 wt % or less based on the weight of the hydrophilic urethane prepolymer (UP), and
   wherein the chlorine content derived from the chlorine-containing organic compound is a sum of chlorine contents derived from the following compounds (1) to (14), a reaction product between compound (1) and (B), a reaction product between compound (2) and (B), a reaction product between compound (7) and (B) and a reaction product between compound (8) and (B):
   Compound (1): A compound represented by the following general formula (I):

$$OCNCH_2(CF_2)_nCH_2OCOCl \quad (I)$$

wherein n represents an integer of 1 to 20;
   Compound (2): A compound represented by the following general formula (II):

$$OCNCH_2(CF_2)_nCH_2Cl \quad (II)$$

wherein n represents an integer of 1 to 20;
   Compound (3): A compound represented by the following general formula (III):

$$ClOCOCH_2(CF_2)_nCH_2OCOCl \quad (III)$$

wherein n represents an integer of 1 to 20;
   Compound (4): A compound represented by the following general formula (IV):

$$ClCH_2(CF_2)_nCH_2Cl \quad (IV)$$

wherein n represents an integer of 1 to 20;
   Compound (5): A compound represented by the following general formula (V):

$$O(CH_2CH_2Cl)_2 \quad (V);$$

Compound (6): A compound represented by the following general formula (VI):

$$ClOCO(CH_2CH_2OCH_2)_2OCH_3 \quad (VI);$$

Compound (7): A compound represented by the following general formula (VII):

$$OCN(CF_2)_nOCOCl \quad (VII)$$

wherein n represents an integer of 1 to 22;
   Compound (8): A compound represented by the following general formula (VIII):

$$OCN(CF_2)_nCl \quad (VIII)$$

wherein n represents an integer of 1 to 22;
   Compound (9): A compound represented by the following general formula (IX):

$$ClOCO(CF_2)_nOCOCl \quad (IX)$$

wherein n represents an integer of 1 to 22;
   Compound (10): A compound represented by the following general formula (X):

$$Cl(CF_2)_nCl \quad (X)$$

wherein n represents an integer of 1 to 22;
   Compound (11): A compound represented by the following general formula (XI):

$$O(CH_2CH_2OCOCl)_2 \quad (XI);$$

Compound (12): A compound represented by the following general formula (XII):

$$ClOCOCH_2CH_2OCH_2CH_2OCOCl \quad (XII);$$

Compound (13): A compound represented by the following general formula (XIII)

$$ClCH_2CH_2OCH_2CH_2OCOCl \quad (XIII);$$

and
   Compound (14): A compound represented by the following general formula (XIV):

$$ClCH_2CH_2OCH_2CH_2OCH_3 \quad (XIV).$$

2. The medical adhesive according to claim 1, wherein a isocyanate group content in the hydrophilic urethane prepolymer (UP) based on the weight of the hydrophilic urethane prepolymer (UP) is 1 to 10 wt %.

3. The medical adhesive according to claim 1, wherein the polyol component (B) is a polyol comprising a polyether polyol.

4. The medical adhesive according to claim 1, wherein the hydrophilic polyol (B1) is a polyether polyol having an oxyethylene group content of 30 to 100 wt %.

5. The medical adhesive according to claim 1, wherein the polyol component (B) is a mixture of a random co-adduct of ethylene oxide and propylene oxide to a diol and a polypropylene glycol.

6. The medical adhesive according to claim 1, for use in bonding a body tissue.

7. The medical adhesive according to claim 6, wherein the body tissue is at least one tissue selected from the group consisting of blood vessel, heart, respiratory organ and digestive organ.

* * * * *